United States Patent [19]

Merger et al.

[11] 4,273,938
[45] Jun. 16, 1981

[54] PREPARATION OF N-SUBSTITUTED CARBOXYLIC ACID AMIDES

[75] Inventors: Franz Merger, Frankenthal; Gerhard Nestler, Ludwigshafen; Uwe Kempe, Limburgerhof, all of Fed. Rep. of Germany

[73] Assignee: BASF Aktiengesellschaft, Fed. Rep. of Germany

[21] Appl. No.: 6,524

[22] Filed: Jan. 25, 1979

[30] Foreign Application Priority Data

Feb. 23, 1978 [DE] Fed. Rep. of Germany ...... 2807659

[51] Int. Cl.$^3$ .................. C07C 102/08; C07C 102/00
[52] U.S. Cl. .................................... 564/124; 564/161; 564/192
[58] Field of Search ........... 260/561 N, 561 R, 558 R; 564/124

[56] References Cited

U.S. PATENT DOCUMENTS

| | | | |
|---|---|---|---|
| 2,773,097 | 12/1956 | Albert | 260/563 |
| 3,023,242 | 2/1962 | Bornemann et al. | 260/561 N |
| 3,041,375 | 6/1962 | Heiny | 260/561 N |
| 3,670,021 | 6/1972 | Goetz et al. | 260/561 R |
| 3,674,848 | 7/1972 | Schoenbrunn et al. | 260/561 R |
| 3,879,457 | 4/1975 | Hensel et al. | 260/561 R |
| 3,887,618 | 6/1975 | Hein | 260/561 N |
| 3,980,662 | 9/1976 | Watanabe et al. | 260/561 R |
| 4,101,577 | 7/1978 | Smathers | 260/561 R |

FOREIGN PATENT DOCUMENTS 1196185 7/1965 Fed. Rep. of Germany.

OTHER PUBLICATIONS

Houben-Weyl Methoden der Organisher Chemie, vol. 11/1, pp. 994–996.
Ullmanns Encyklopädie der Technischen Chem., vol. 5 (1954), p. 108.
Ullmanns Encykopädie der Technischen Chem. Supp., p. 136 (1970).
Organic Reactions, vol. 17 (1969), pp. 213–325.
Organikum, 1975, p. 472, Krauch et al., Reactionen der Org. Chem., 5th ed., p. 544.
Olah et al., Friedel–Crafts and Related Reactions (1964), vol. II, part 1, p. 201.
Glikmans et al., Bull. Soc. Chim., France, 1966, pp. 1376–1388.
Calmon et al., Ion Exchangers in Organic and Biochemistry; Interscience; 1957, pp. 658–687.
Kirk–Othmer, Encyclopedia of Chemical Technology, vol. 11 (1967), p. 891.

*Primary Examiner*—Arthur P. Demers
*Attorney, Agent, or Firm*—Keil & Witherspoon

[57] ABSTRACT

N-substituted carboxylic acid amides are prepared by reacting cyano compounds with olefins and water in the presence of cation exchangers containing sulfonic acid groups. The end products I are starting materials for the preparation of dyes, pesticides, emulsifiers, dispersants, stabilizers, textile auxiliaries and printing assistants.

13 Claims, No Drawings

PREPARATION OF N-SUBSTITUTED CARBOXYLIC ACID AMIDES

The present invention relates to a process for the preparation of N-substituted carboxylic acid amides by reacting cyano compounds with olefins and water in the presence of cation exchangers containing sulfonic acid groups.

Houben-Weyl, Methoden der Organischen Chemie, Volume 11/1, pages 994–996 discloses that hydrogen cyanide or nitriles may be reacted with olefins in the presence of sulfuric acid to give, respectively, N-formylamines and N-substituted carboxylic acid amides. Hydrolysis then gives the corresponding amines; this elegant method permits the preparation of numerous amines, especially tert.-alkylamines, which can only be prepared with difficulty, if at all, by other methods. In the Examples, the reaction is carried out with an equimolar amount, or an excess, of sulfuric acid.

Preferably, sulfuric acid is used in the reaction, as stated in Organic Reactions 17 (1969), 213–325, but acetic acid, hydrochloric acid, benzenesulfonic acid, toluenesulfonic acid, propionic acid, boron trifluoride hydrate, polyphosphoric acid, fluoboric acid, ferrocyanic acid, phosphoric acid and formic acid have also already been used as catalysts (loc. cit., pages 257–324).

A substantial disadvantage of these prior art processes is the corrosiveness of the acids and the large amount of acid required, as a rule from 1 to 4 moles of acid per mole of olefin, as is also indicated in German Published Applications DAS No. 1,196,185 and DAS No. 2,144,230. The presence of the acid necessitates expensive working up of the reaction mixture, with pollution of the environment. To isolate the amides, the mixture must be diluted with water and neutralized, which entails the loss of the acid and pollution of the effluent by the large amounts of salt formed. After dilution and neutralization, the mixture must be filtered or extracted with a suitable solvent, for example ether (German Published Application DAS No. 1,196,185). In another method of working up, dilution of the reaction mixture is followed by extraction with suitable phosphoric acid esters or urea derivatives, in which case the extract may require washing with water to remove traces of acid (German Published Application DAS No. 2,144,230). The recovery of the extractant, and the isolation of the amide, is in particular achieved by distillation under reduced pressure.

All these processes are unsatisfactory in respect of space-time yield and of simplicity and economy of operation, especially with respect to working up of the reaction mixture.

We have found that N-substituted carboxylic acid amides of the formula

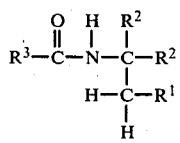

where $R^1$ and the individual radicals $R^2$ are identical or different and each is an aliphatic radical, two of the radicals $R^1$ and $R^2$ may also each be hydrogen and $R^3$ is hydrogen or an aliphatic, araliphatic or aromatic radical, are obtained in an advantageous manner by reaction of olefins with cyano compounds if an olefin of the formula

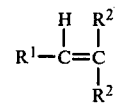

where $R^1$ and $R^2$ have the above meanings, is reacted with a cyano compound of the formula

where $R^3$ has the above meaning, and with water, in the presence of from 10 to 80 percent by weight, based on starting material II, of an organic cation exchanger containing sulfonic acid groups.

Where acetonitrile and isobutylene are used, the reaction can be represented by the following equation:

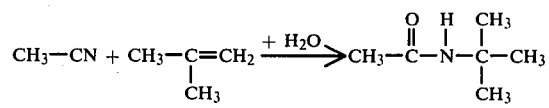

Compared to the conventional processes, the process according to the invention surprisingly permits simpler, more economical and environmentally less polluting preparation of a large number of N-substituted carboxylic acid amides in good space-time yield, particularly on an industrial scale and in continuous operation and, in some cases, in better yield and greater purity. The catalysts are substantially easier to isolate and re-utilize. All these advantages of the process according to the invention are surprising, especially in view of the fact that only a small amount of catalyst is used.

The starting material II can be reacted with the cyano compound III in the stoichiometric amount or in excess, preferably in a ratio of from 0.1 to 10, especially from 0.5 to 5, moles of starting material III per mole of starting material II. Water is employed in the stoichiometric amount or in an excess, advantageously in a ratio from 0.2 to 5, preferably from 0.5 to 2, moles of water per mole of starting material II.

Preferred starting materials II and III and, accordingly, preferred end products I are those where $R^1$ and the individual radicals $R^2$ may be identical or different and each is alkyl of 1 to 9, especially of 1 to 4, carbon atoms, two of the radicals $R^1$ and $R^2$ may also each be hydrogen, and $R^3$ is hydrogen, alkyl of 1 to 9, especially of 1 to 4, carbon atoms, alkenyl of 2 to 9, especially of 2 to 4, carbon atoms, alkylphenyl or phenylalkyl of 7 to 12 carbon atoms or phenyl. The above radicals may be substituted by groups which are inert under the reaction conditions, for example alkyl of 1 to 3 carbon atoms. Branched alkenes are preferred as starting materials II.

Instead of the olefins II, compounds which form an olefin, through elimination of water, under the reaction conditions may also be used, for example tertiary or secondary alkanols, advantageously alkanols of the formula

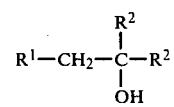

where $R^1$ and $R^2$ have the above meanings. Since water is formed, it is advantageous, in such cases of the reaction according to the invention, to dispense partially or entirely with the addition of water.

Compounds which form an olefin under the reaction conditions but do not eliminate water may also be used in place of the starting materials II; examples are tertiary and secondary alkyl esters and alkyl ethers, advantageously those of the formula

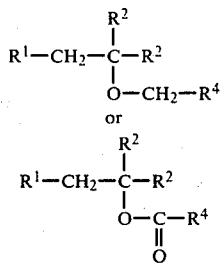

where $R^1$ and $R^2$ have the above meanings and the radicals $R^4$ are each hydrogen or an aliphatic radical, preferably alkyl of 1 to 9, especially of 1 to 4, carbon atoms. In such cases, water must be added to the reaction, since no water is eliminated from the reactants.

The following are examples of olefins which may be used as starting materials II: n-pent-1-ene, n-hex-1-ene, n-hept-1-ene, n-oct-1-ene, n-non-1-ene, n-dec-1-ene, n-undec-1-ene, n-dodec-1-ene, propene and n-but-1-ene; the above alkenes, substituted in the 2-position or 3-position or 4-position by methyl, ethyl, n-propyl, isopropyl, n-butyl, isobutyl, sec.-butyl or tert.-butyl; 2,3-dimethyl-n-butene, 3,3-dimethyl-n-butene, 2,5-dimethylheptene, 3,3-dimethylheptene, 2,3,4-trimethylheptene, 2,4-dimethylheptene, 2,3-dimethylheptene, 4,4-dimethylheptene, 2,3-diethylhexene, 4,4-dimethylhexene, 2,3-dimethylhexene, 2,4-dimethylhexene, 2,5-dimethylhexene, 3,3-dimethylhexene, 3,4-dimethylhexene, 2-methyl-3-ethylpentene, 3-methyl-3-ethylpentene, 2,3,3-trimethylheptene, 2,4,4-trimethylpentene, 2,3,3-trimethylpentene, 2,3,4-trimethylpentene and 2,3,3,4-tetramethylhexene; similar alkenes where the double bond is in the 2-position or 3-position of the molecule; branched alkenes as obtained, in the form of mixtures, on dimerizing isobutylene or n-butene (ie. octenes) or on trimerizing isobutylene or n-butene (ie. dodecenes) or propylene (ie. nonenes) or on tetramerizing propylene (ie. dodecenes). The following are preferred: isobutylene, n-butene, propene, 2,3-dimethyl-but-1-ene, 2-methyl-but-1-ene, 2-methyl-but-2-ene, 2-methyl-pent-2-ene, 3-methyl-hex-3-ene, 2-methyl-hept-1-ene, 2,3-dimethyl-pent-1-ene, 2,3-dimethyl-hexene and 2,4,4-trimethylpent-1-ene.

The tertiary and secondary alkanols, alkyl esters and alkyl ethers corresponding to the above olefins II may also be used, preferred examples being tert.-butanol, isopropanol, sec.-butanol, tert.-butyl acetate and methyl tert.-butyl ether.

Examples of suitable cyano compounds III are: hydrogen cyanide, isopropioninitrile, butyronitrile, isobutyronitrile, sec.-butyronitrile, tert.-butyronitrile, acetonitrile, propionitrile, acrylonitrile, benzonitrile and phenylacetonitrile.

The reaction is in general carried out at from 50° to 150° C., preferably from 70° to 140° C., especially from 75° to 125° C., under reduced pressure, superatmospheric pressure or atmospheric pressure, batchwise or continuously. In continuous operation, the residence time is preferably from 0.5 to 20, especially from 1 to 10, hours and the throughput is from 1 to 60, especially from 2 to 30, kilograms of starting material II per kilogram of catalyst per hour. The exchanger is employed in an amount of from 10 to 80, preferably from 40 to 70, percent by weight, based on starting material II.

The catalysts used are organic cation exchangers containing sulfonic acid groups, advantageously resins consisting of sulfonated polystyrene or of sulfonated cross-linked styrene copolymers, bifunctional condensation resins containing sulfonic acid groups, phenolsulfonic acid resins and phenol-formaldehyde resins containing sulfonic acid groups. The use of a sulfonated styrene/divinylbenzene copolymer exchanger is preferred. The exchanger is in the acid form, not in the salinated form. The catalyst may be coarse or fine, and advantageously has a particle size of from 0.005 to 2, preferably from 0.02 to 1, millimeter. Advantageously, its structure is gel-like. Examples of suitable exchanger resins are those commercially available under the name ®LEWASORB A-10. Other commercial resins which may be used are ®Amberlit IR-120, ®Dowex 50, ®Lewatit S-100, ®Nalcite HCR, ®Permutit RS, ®Wofatit KPS-200, ®Amberlyst-15, ®Lewatit SC-108 and ®Lewatit SPC-108. Before use, the resins are advantageously dehydrated in the conventional manner, for example by heating under reduced pressure. However, they can also be dehydrated by displacing the water with hydrophilic organic liquids and then heating at 100° C. under reduced pressure, or by azeotropic distillation with an organic liquid.

During the reaction, the catalyst is advantageously in suspension, as a rule in the mixture undergoing reaction. Advantageously, the catalyst is suspended in part of the liquid starting mixture of cyano compound III and olefin II, with thorough mixing. It is advantageous not to use an additional solvent, though under certain circumstances solvents which are inert under the reaction conditions may be used, for example to lower the viscosity of the reaction mixture. Examples of suitable solvents are aliphatic and cycloaliphatic hydrocarbons, eg. heptene, nonane, gasoline fractions boiling in the range from 70° to 190°, cyclohexane, methylcyclohexane, decalin, petroleum ether, hexane, naphtha, 2,2,4-trimethylpentane, 2,2,3-trimethylpentane, 2,3,3,3-trimethylpentane and octane; halohydrocarbons, especially chlorohydrocarbons, eg. tetrachloroethylene, 1,1,2,2-tetrachloroethane, 1,1,1,2-tetrachloroethane, dichloropropane, methylene chloride, dichlorobutane, chloroform, carbon tetrachloride, tetrachloroethane, 1,1,1-trichloroethane, 1,1,2-trichloroethane, trichloroethylene, pentachloroethane, cis-dichloroethylene, 1,2-dichloroethane and 1,1-dichloroethane; diethyl ether, tetrahydrofuran and dioxane, and mixtures of these. Advantageously, the solvent is used in an amount of from 5 to 500 percent by weight, preferably from 20 to 100 percent by weight, based on starting material II. In the case of mixtures of starting material II, for example obtained from petroleum cracking, the saturated hydrocarbons present in the mixture can be used as the solvent present in the suspension. The amount of initially taken starting mixture and/or organic solvent is advantageously chosen so that the amount of catalyst suspended in the reaction mixture formed is from 1 to 30, preferably from 10 to 20, percent by weight, based on the weight of the total liquid mixture in the reaction space. Advantageously, the batch is mixed throughout the reaction, preferably by stirring at not less than 100, advantageously from 200 to 2,000, especially from 300 to 1,000, rpm. In the case of mixing equipment without a stirrer, for example when mixing by means of an inert gas such as nitrogen, it is preferred to work with equipment which introduces a shearing energy corresponding to the above speed of stirring. In this way, a finely dispersed suspension is obtained. Provided the above mixing conditions are used, a wide range of conventional stirring equipment may be employed, eg. injectors, ball jets, vortex jets, turbine stirrers, mixing nozzles, Lechler mixing nozzles, paddle stirrers, anchor stirrers, bar-type stirrers, propeller stirrers, Cramer stirrers, vibro-mixers, finger-type stirrers, crossbeam stirrers, gyratory stirrers, grid stirrers, flat stirrers, spiral turbines, scoop stirrers, planetary stirrers, centrifugal gyratory stirrers, rotating atomizers, ejectors, triangular stirrers, hollow stirrers, tubular stirrers and impeller stirrers. Apparatus and equipment such as stirred kettles, stirred kettle cascades, flow tubes, air-lift type stirring units, homogenizing equipment, gyratory mixers, turbo-mixers, emulsifying centrifuges, ultrasonic tubes, flow mixers, rotating drums, chamber reactors, circulatory reactors, loop reactors, cellular reactors, screw reactors and bubble columns may also be used; if only for economic reasons, stirred kettles are preferred.

The reaction may be carried out as follows: a mixture of starting materials II and III, water and catalyst, with or without solvent, is reacted at the reaction temperature, in the case of batchwise operation for from 1 to 6 hours, the catalyst being kept suspended in the starting mixture or reaction mixture. The end product is then isolated from the reaction mixture in the conventional manner, for example by filtration and distillation. In batchwise operation, the ion exchanger may be separated off by, for example, filtering, centrifuging or sedimenting, after which it can be re-used directly.

In an advantageous embodiment of the continuous method of operation, the mixture of the starting materials and of the catalyst, with or without solvent, is passed continuously into a reactor containing a suspension of the catalyst in the reaction mixture, and at the same time an appropriate amount of suspension is continuously withdrawn through a filter. Advantageously, this filtration occurs before the suspension leaves the reactor. Suitable filters are acid-resistant filter cloths, wire gauze filters and sintered metal filters, provided the mesh sizes or pore diameters are less than the size of the catalyst particles. Decanting equipment can also be used advantageously for separating off the catalyst. As a rule, the catalyst which has been separated off is returned continuously to the reaction.

The end products I obtainable by the process of the invention are valuable starting materials for the preparation of dyes, pesticides, emulsifiers, dispersants, stabilizers, textile auxiliaries and printing assistants. Regarding their use, reference may be made to the above publications and to Ullmanns Encyklopädie der technischen Chemie, Volume 5, page 108 and Supplementary Volume, page 136.

In the Examples which follow, parts are by weight.

EXAMPLE 1

A suspension of 123 parts of acetonitrile, 74 parts of tert.-butanol and 25 parts of the exchanger resin is prepared in a stirred autoclave by stirring at 500 rpm, and is heated at 120° C. The exchanger resin is a sulfonated styrene/divinylbenzene copolymer resin which before use has been dehydrated for 20 hours at 100° C. under reduced pressure; it has a gel structure, and a particle size of from 20 to 200 micrometers. After stirring for 3 hours at 120° C., the catalyst is separated off and the filtrate is distilled. The residue obtained consists of 175 parts of N-tert.-butylacetamide (89% of theory, based on tert.-butanol employed), of melting point 97°-98° C.

EXAMPLE 2

A suspension of 123 parts of acetonitrile, 56 parts of isobutene, 18 parts of water and 30 parts of exchanger resin is prepared in a stirred autoclave by stirring at 500 rpm, and is heated at 120° C. The exchanger resin is a sulfonated styrene/divinylbenzene copolymer resin which before use has been dehydrated for 20 hours at 100° C. under reduced pressure; it has a gel structure, and a particle size of from 20 to 200 micrometers. After stirring for 4 hours at 120° C., the catalyst is separated off and the filtrate is distilled. The residue obtained consists of 187 parts of N-tert.-butylacetamide (95% of theory, based on isobutene), of melting point 97°-98° C.

EXAMPLE 3

A suspension of 148 parts of tert.-butanol, 180 parts of hydrogen cyanide and 70 parts of exchanger resin is prepared in a stirred autoclave by stirring at 500 rpm, and is heated at 110° C. The exchanger resin is a sulfonated styrene/divinylbenzene copolymer resin which before use has been dehydrated for 20 hours at 100° C. under reduced pressure; it has a gel structure, and a particle size of from 10 to 300 micrometers. After stirring for 2 hours at 110° C., the catalyst is separated off and the filtrate is distilled. The residue obtained consists of 165 parts of N-tert.-butylformamide (82% of theory) of boiling point 82°-85° C./14 mbar.

EXAMPLE 4

A suspension of 112 parts of isobutene, 216 parts of hydrogen cyanide, 36 parts of water and 70 parts of exchanger resin is prepared in a stirred autoclave by stirring at 500 rpm, and is heated at 80° C. The exchanger resin is a sulfonated styrene/divinylbenzene copolymer resin which before use has been dehydrated for 20 hours at 100° C. under reduced pressure; it has a gel structure, and a particle size of from 10 to 300 micrometers. After stirring for 2 hours at 80° C., the catalyst is separated off and the filtrate is distilled. The residue obtained consists of 185 parts of N-tert.-butylformamide (92% of theory) of boiling point 82°-85° C./14 mbar.

EXAMPLE 5

A suspension of 200 parts of acetonitrile, 120 parts of tert.-butanol and 50 parts of exchanger resin is prepared in a stirred autoclave by stirring at 500 rpm, and is heated at 120° C. The exchanger resin is a sulfonated styrene/divinylbenzene copolymer resin which before use has been dehydrated for 20 hours at 100° C. under reduced pressure; it has a gel structure, and a particle size of from 20 to 200 micrometers. After stirring for 3 hours at 120° C., 40 parts of acetonitrile and 25 parts of tert.-butanol are introduced per hour, at 120° C., and correspondingly 65 parts of suspension are removed by filtration through a take-off line fitted with a metal filter, and are passed to a distillation stage. Over 10 hours' operation, 585 parts of N-tert.-butylacetamide (88% of theory) of melting point 97°–98° C. are obtained after removing the unconverted starting materials by distillation.

We claim:

1. A process for the preparation of an N-substituted carboxylic acid amide of the formula

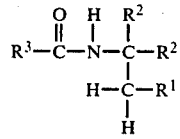  I where $R^1$ and the individual radicals $R^2$ are identical or different and each is an aliphatic radical, two of the radicals $R^1$ and $R^2$ can also each be hydrogen, and $R^3$ is hydrogen or an aliphatic, araliphatic or aromatic radical, by reaction of an olefin with a cyano compound, wherein an olefin of the formula

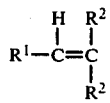  II where $R^1$ and $R^2$ have the above meanings, is reacted with a cyano compound of the formula

 $R^3CN$   III where $R^3$ has the above meaning, and with water, in the presence of from 10 to 80 percent by weight, based on starting material II, of an organic cation exchanger containing sulfonic acid groups.

2. A process as claimed in claim 1, wherein the reaction is carried out with from 0.1 to 10 moles of starting material III per mole of starting material II.

3. A process as claimed in claim 1, wherein the reaction is carried out with from 0.2 to 5 moles of water per mole of starting material II.

4. A process as set forth in claim 1, wherein the reaction is carried out with compounds which, under the reaction conditions, form an olefin by elimination of water, and no water is added.

5. A process as set forth in claim 1, wherein the reaction is carried out with tertiary or secondary alkyl esters and alkyl ethers of the formula

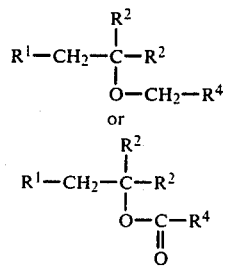

where $R^1$ and $R^2$ have the above meanings and each of the radicals $R^4$ is hydrogen or an aliphatic radical, in place of the starting materials II.

6. A process as set forth in claim 1, wherein the reaction is carried out at from 50° to 150° C.

7. A process as set forth in claim 1, wherein the reaction is carried out at from 70° to 140° C.

8. A process as set forth in claim 1, wherein the reaction is carried out continuously with a residence time of from 0.5 to 20 hours and a throughput of from 1 to 60 kilograms of starting material II per kilogram of catalyst per hour.

9. A process as set forth in claim 1, wherein the reaction is carried out with from 40 to 70 percent by weight, based on starting material II, of the exchanger.

10. A process as set forth in claim 1, wherein the reaction is carried out with a resin consisting of sulfonated polystyrene, a sulfonated, crosslinked styrene copolymer, a bifunctional condensation resin containing sulfonic acid groups, a phenolsulfonic acid resin or a phenol-formaldehyde resin containing sulfonic acid groups.

11. A process as set forth in claim 1, wherein the reaction is carried out with a catalyst having a particle size of from 0.005 to 2 millimeters.

12. A process as set forth in claim 1, wherein the reaction is carried out with the catalyst present in suspension in the mixture undergoing reaction in an amount of from 1 to 30 percent by weight, based on the weight of the total liquid mixture in the reaction space.

13. A process as set forth in claim 1, wherein the reaction is carried out while stirring at from 200 to 2,000 rpm or introducing shearing energy corresponding to the above speed of stirring.

* * * * *